US00PP21410P2

(12) United States Plant Patent
Perkins

(10) Patent No.: US PP21,410 P2
(45) Date of Patent: Oct. 19, 2010

(54) ***SALVIA* PLANT NAMED 'MES SCAR'**

(50) Latin Name: ***Salvia*×hybrid**
Varietal Denomination: Mes Scar

(75) Inventor: Ralph T. Perkins, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 64 days.

(21) Appl. No.: 12/313,158

(22) Filed: Nov. 18, 2008

(51) Int. Cl.
*A01H 5/00* (2006.01)

(52) U.S. Cl. ..... Plt./475

(58) Field of Classification Search ..... Plt./475
See application file for complete search history.

(56) References Cited

U.S. PATENT DOCUMENTS

| | | | | |
|---|---|---|---|---|
| PP19,702 | P2 * | 2/2009 | Unger | Plt./475 |
| PP19,792 | P2 * | 3/2009 | Danziger | Plt./475 |
| 2009/0276928 | P1 * | 11/2009 | Bernabe | Plt./475 |

OTHER PUBLICATIONS

Upov rom gtitm computer software gti jouve retrieval 2009/04 citation for 'mes scar'.*

* cited by examiner

*Primary Examiner*—Wendy C. Haas
(74) *Attorney, Agent, or Firm*—S. Matthew Edwards

(57) ABSTRACT

A new *Salvia* plant named 'Mes Scar,' particularly distinguished by red-scarlet flower color, upright, well branched, dense and bushy habit, medium green foliage and large sized flowers that are early flowering.

1 Drawing Sheet

Latin name of the genus and species of the plant claimed: *Salvia* ×hybrid.

Varietal denomination: 'Mes Scar'.

BACKGROUND OF THE NEW PLANT

The present invention comprises a new *Salvia*, botanically known as *Salvia* ×hybrid, and hereinafter referred to by the variety name 'Mes Scar'.

'Mes Scar' is a product of a planned breeding program. The new cultivar 'Mes Scar' has red-scarlet flower color, upright, well branched, dense and bushy habit, medium green foliage and large sized flowers that are early flowering.

'Mes Scar' originated from an open pollination cross in a controlled breeding program in Gilroy, Calif. USA. The female parent was an unpatented, proprietary hybrid seedling (*Salvia greggi x. S. micorphylla*) identified as '77-2' with crimson color. '77-2' has smaller and darker foliage and a taller, less compact habit than 'Mes Scar.' The male parent of 'Mes Scar' was unknown.

'Mes Scar' was selected as one flowering plant within the progeny of the stated cross in September 2005 in a controlled environment in Gilroy, Calif. USA. The pollination took place in July 2004 and the seed sowing in May 2005.

The first act of asexual reproduction of 'Mes Scar' was accomplished when vegetative cuttings were taken from the initial selection in the September 2005 in a controlled environment in Gilroy, Calif. USA.

Horticultural examination of plants grown from cuttings of the plant initiated in September 2005 in Gilroy, Calif. USA, and continuing thereafter, has demonstrated that the combination of characteristics as herein disclosed for 'Mes Scar' are firmly fixed and are retained through successive generations of asexual reproduction.

'Mes Scar' has not been observed under all possible environmental conditions. The phenotype may vary significantly with variations in environment such as temperature, light intensity and day length.

A Plant Breeder's Right for this cultivar was applied for in Canada on Dec. 24, 2007. 'Mes Scar' has not been made publicly available more than one year prior to the filing of this application.

DESCRIPTION OF THE DRAWINGS

The accompanying photographic drawing shows typical flower and foliage characteristics of 'Mes Scar' with colors being as true as possible with an illustration of this type. The photographic drawing shows a flowering potted plant of the new variety and a close-up of the flowers, growing in 4 inch pots. This plant was grown and photographed in Gilroy, Calif. USA in June 2008. The plant was about 3 months old.

DETAILED BOTANICAL DESCRIPTION

The measurements were taken on plants growing in Gilroy, Calif. USA in April 2008. The plants were growing in gallon pots in a greenhouse trial. These plants were about 4-5 months old.

Color Chart used: Royal Horticultural Society Colour Chart (R.H.S.) 2001.

BRIEF SUMMARY OF INVENTION

The following observations, measurements, and comparisons describe plants grown Gilroy, Calif. USA. The following traits have been repeatedly observed and are determined to be basic characteristics of the new variety. The combination of these characteristics distinguishes this *Salvia* as a new and distinct variety.

TABLE 1

DIFFERENCES BETWEEN THE NEW CULTIVAR 'MES SCAR' AND A SIMILAR VARIETY

| | 'Mes Scar' | 'Navajo Bright Red' (Unpatented) |
|---|---|---|
| Floriferousness | More flowers | Fewer flowers |
| Compactness | More compact | Less compact |
| Plant height | Shorter | Taller |

Plant:

*Form, growth and habit.*—Upright, well branching, dense and bushy.
*Plant height.*—35-38 cm.
*Plant height (inflorescence included).*—43-45 cm.
*Plant width.*—45-50 cm.

Foliage:

*Type.*—Simple, opposite.
*Immature, leaf color, upper surface.*—Closest to RHS 146A.
*Lower surface.*—Closest to RHS 137C.
*Mature, leaf color, upper surface.*—Closest to RHS 147A and B.
*Lower surface.*—Closest to RHS 137C.
*Length.*—3.6-6.2 cm.
*Width.*—1.7-2.7 cm.
*Shape.*—Obovate.
*Base shape.*—Attenuate.
*Apex shape.*—Obtuse to slightly mucronulate.
*Margin.*—Crenulate.
*Texture, upper surface.*—Hispid; glandular hairs.
*Texture, lower surface.*—Hispid; glandular hairs.
*Fragrant.*—Heavily "sage" like.
*Color of veins, upper surface.*—RHS 144A.
*Color of veins, lower surface.*—RHS 144A.
*Petioles color.*—RHS 144A.
*Petioles length.*—1.8-2.3 cm.
*Diameter of petiole.*—0.1 cm.
*Texture.*—Hispid; glandular hairs.

Stem:

*Number of main branches per plant.*—3-4.
*Number of leaves per stem.*—12-16.
*Color of stem.*—RHS 146C.
*Length of stem.*—35-40 cm.
*Diameter.*—0.3-0.4 cm.
*Length of internodes.*—4-5 cm.
*Texture.*—Hispid; glandular hairs.

Inflorescence:

*Type.*—Terminal raceme.
*Blooming habit.*—Flowers continuously from spring through the fall.
*Number of racemes per plant.*—30-45.
*Duration of flowering.*—Continuous flowering throughout the summer.
*Color of peduncle.*—RHS 146C.
*Length of peduncle.*—5-11 cm.
*Peduncle diameter.*—0.2 cm.
*Texture.*—Hispid; glandular hairs.
*Color of pedicel.*—RHS 146C; RHS 177B anthocyanin overlay.
*Length of pedicel.*—0.3-0.4 cm.
*Diameter of pedicel.*—0.1 cm.
*Texture.*—Hispid; glandular hairs.

Corolla:

*Form.*—Single: bilabiate; with one upper lip, and one lower lip with three lobes consisting one a large mid-lobe and 2 small lateral lobes; fused at base; upper lip wraps around the pistil.
*Lastingness of individual bloom on the plant.*—5-7 days.
*Fragrance.*—"Sage" like.
*Immature florets general color, upper surface.*—Closest to RHS 46B.
*Lower surface.*—RHS 45C.
*Mature florets vertical height of floret.*—1.8-2.1 cm.
*Horizontal width of floret.*—1.7-2.0 cm.
*Depth of floret.*—2.2-2.5 cm.
*Color upper lip, upper surface.*—Between RHS 46B and C but appears brighter because of the RHS 46A color of the villous hairs.
*Color upper lip, lower surface.*—RHS N155C.
*Length of upper lip.*—0.9-1.1 cm.
*Width of upper lip.*—0.3 cm.
*Shape.*—Obovate.
*Apex shape.*—Obtuse.
*Margin.*—Entire.
*Texture, outer surface.*—Papillose; villous hairs of RHS 46A at the apex.
*Inner surface.*—Glabrous.
*Color lower lip, mid-lobe, upper surface.*—RHS 46B; small blotch of RHS N155B basally.
*Color lower lip, mid-lobe, lower surface.*—RHS 45C; RHS N155B basally.
*Length of lower lip, mid-lobe.*—1.5-1.6 cm.
*Width of lower lip, mid-lobe.*—0.9-1.0 cm.
*Shape.*—Obcordate.
*Apex shape.*—Emarginate.
*Margin.*—Entire.
*Texture, upper surface.*—Papillose.
*Lower surface.*—Slightly hispid.
*Color lower lip, lateral lobe, upper surface.*—Between RHS 46B and C.
*Color lower lip, lateral lobe, lower surface.*—RHS 45C.
*Length of lower lip, lateral lobe.*—0.7-0.8 cm.
*Width of lower lip, lateral lobe.*—0.35 cm.
*Petal shape.*—Oblong.
*Apex shape.*—Rounded.
*Margin.*—Entire.
*Texture, upper surface.*—Papillose.
*Lower surface.*—Slightly hispid.
*Corolla, color, outer surface.*—RHS 46C.
*Inner surface.*—RHS 55C with slight stripes of RHS N155B.
*Length of corolla.*—2.3-2.6 cm.
*Width of corolla.*—0.7 cm at the widest portion.
*Texture, outer upper surface.*—Hispid.
*Texture, outer lower surface.*—Glabrous.
*Texture, inner surfaces.*—Glabrous.

Bud (just before opening):

*Color.*—Closest to RHS 187A but lighter.
*Length.*—1.5-1.7 cm.
*Width.*—0.5 cm.
*Shape.*—Tubular to oblong.

Calyx:

*Number of sepals.*—2, fused into a tube form.
*Color of sepals, upper surface.*—RHS 144C ground color; mid veins heavily colored RHS 187A with anthocyanins on upper sepal; fading to RHS 184B on the lower sepal.

*Inner surface.*—RHS 147C.
*Length of sepals.*—1.0-1.1 cm.
*Width of sepals.*—0.3-0.5 cm.
*Sepal shape.*—Broadly linear.
*Apex shape.*—Acute.
*Margin.*—Entire.
*Texture, outer surface.*—Hispid; glandular hairs.
*Inner surface.*—Glabrous.

Reproductive organs:

*Pistil.*—1.
*Length.*—2.3-2.4 cm.
*Style color.*—RHS N155B but whiter.
*Style length.*—2.0-2.2 cm.
*Stigma color.*—One lobe is RHS N74B and the other is RHS N74D.
*Stamens.*—2.
*Color of filaments.*—RHS 155C.
*Anther color.*—RHS 16B.
*Anther length.*—0.2 cm.
*Color of pollen.*—RHS 13B
*Pollen amount.*—Moderate.
*Fertility/seed set.*—Not observed on this hybrid.

Disease/pest resistance: Disease resistance or susceptibility has not been observed on this hybrid.

What is claimed is:

1. A new and distinct variety of *Salvia* plant named 'Mes Scar,' substantially as illustrated and described herein.

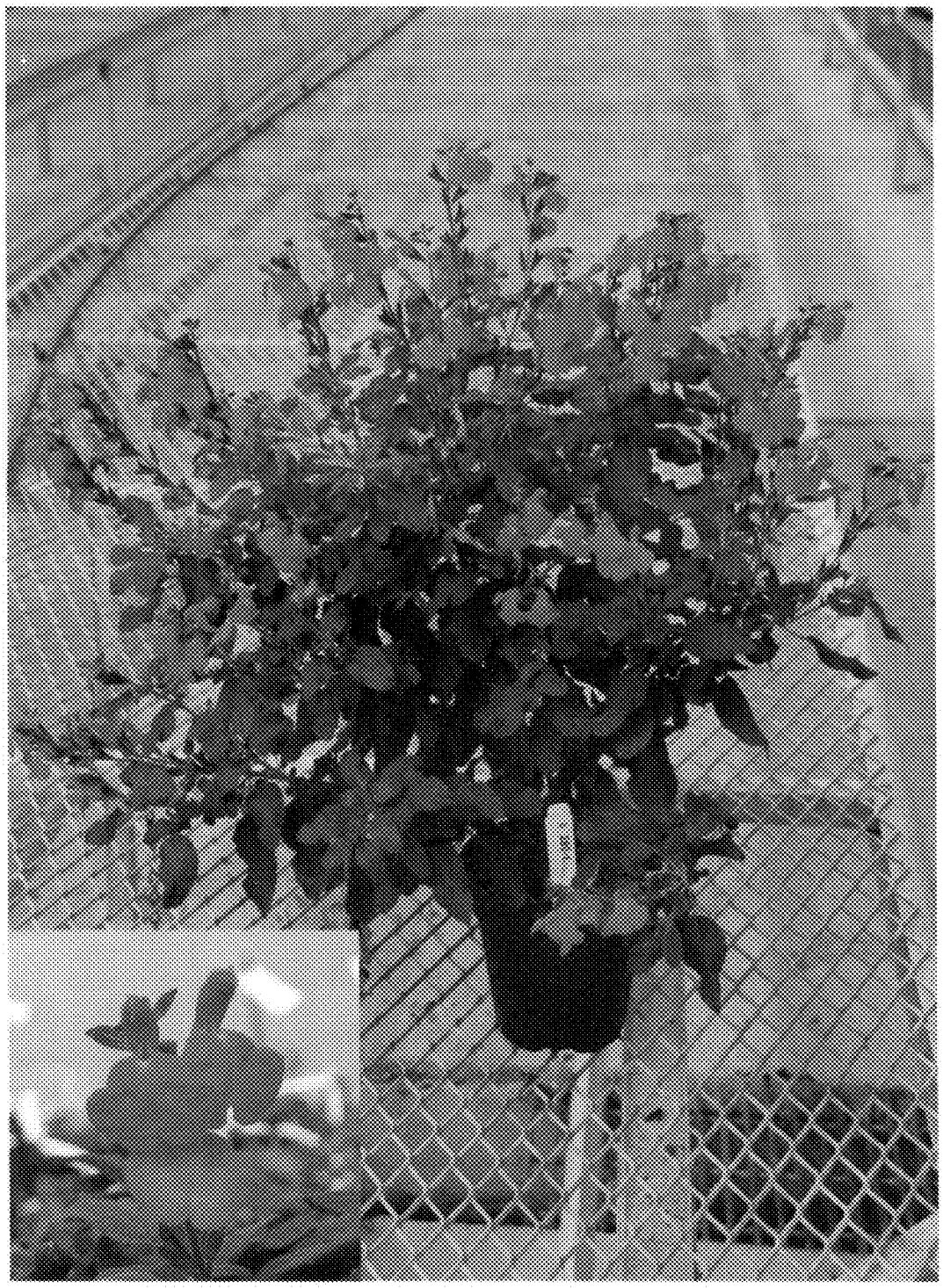

* * * * *